United States Patent
Kim et al.

(10) Patent No.: US 10,971,758 B2
(45) Date of Patent: *Apr. 6, 2021

(54) ELECTROLYTE ADDITIVE AND LITHIUM SECONDARY BATTERY COMPRISING THE SAME

(71) Applicant: SOULBRAIN CO., LTD., Seongnam-si (KR)

(72) Inventors: Jae Yoon Kim, Seongnam-si (KR); Hyeong Kyu Lim, Seongnam-si (KR); Jong Hyun Lee, Seongnam-si (KR)

( * ) Notice: Subject to any disclaimer, the term of this patent is extended or adjusted under 35 U.S.C. 154(b) by 143 days.

This patent is subject to a terminal disclaimer.

(21) Appl. No.: 16/134,938

(22) Filed: Sep. 18, 2018

(65) Prior Publication Data
US 2019/0089001 A1    Mar. 21, 2019

(30) Foreign Application Priority Data

Sep. 20, 2017  (KR) .................. 10-2017-0121186
Aug. 31, 2018  (KR) .................. 10-2018-0103946

(51) Int. Cl.
| | | |
|---|---|---|
| *H01M 10/0567* | (2010.01) | |
| *H01M 10/0525* | (2010.01) | |
| *H01M 10/0569* | (2010.01) | |
| *H01M 10/0568* | (2010.01) | |
| *C07D 285/15* | (2006.01) | |
| *H01M 10/42* | (2006.01) | |
| *C07C 381/00* | (2006.01) | |
| *C01B 21/086* | (2006.01) | |
| *C07C 311/48* | (2006.01) | |

(52) U.S. Cl.
CPC ....... *H01M 10/0567* (2013.01); *C01B 21/086* (2013.01); *C07C 311/48* (2013.01); *C07C 381/00* (2013.01); *C07D 285/15* (2013.01); *H01M 10/0525* (2013.01); *H01M 10/0568* (2013.01); *H01M 10/0569* (2013.01); *H01M 10/4235* (2013.01); *H01M 2300/0025* (2013.01)

(58) Field of Classification Search
CPC ......... H01M 10/0567; H01M 10/4235; H01M 10/0525; H01M 10/0569; H01M 10/0568; C07C 311/48; C07C 381/00; C07D 285/15; C01B 21/086
See application file for complete search history.

(56) References Cited

U.S. PATENT DOCUMENTS

| | | | | |
|---|---|---|---|---|
| 2012/0244419 A1* | 9/2012 | Kwak | ............... | H01M 10/0567 429/163 |
| 2016/0261000 A1* | 9/2016 | Zhang | ............... | H01M 10/0568 |
| 2019/0089002 A1* | 3/2019 | Kim | ............... | H01M 10/0567 |

FOREIGN PATENT DOCUMENTS

KR    1020090026203 A    3/2009

* cited by examiner

Primary Examiner — Stewart A Fraser
(74) Attorney, Agent, or Firm — Jongkook Park

(57) ABSTRACT

The present invention relates to an electrolyte additive comprising a salt of an anion with $K^+$ or $Na^+$, the anion being derived from a nitrogen atom-containing compound, and a lithium-containing compound for forming a coating film. In addition, the present invention provides a lithium salt, a non-aqueous organic solvent, and the electrolyte additive. The present invention relates to a lithium secondary battery which includes a cathode employing a cathode active material, an anode employing an anode active material, a separator interposed between the cathode and the anode, and the non-aqueous electrolyte.

10 Claims, No Drawings

# ELECTROLYTE ADDITIVE AND LITHIUM SECONDARY BATTERY COMPRISING THE SAME

CROSS-REFERENCE TO RELATED APPLICATIONS

This application claims priority under 35 U.S.C. § 119 to Korean Patent Application No. 10-2017-0121186, filed on Sep. 20, 2017, and Korean Patent Application No. 10-2018-0103946, filed on Aug. 31, 2018 in the Korean Intellectual Property Office, the disclosures of which are incorporated herein by reference in its entirety.

TECHNICAL FIELD

The following disclosure relates to an electrolyte additive and a lithium secondary battery including the electrolyte additive in a non-aqueous electrolyte.

BACKGROUND

In accordance with the recent development of the information and communication industry, electronic devices are becoming smaller, lighter, thinner, and more portable. As a result, there is a growing demand for high energy densification of batteries used as power sources for these electronic devices. As lithium secondary batteries are best able to meet such demand, research thereon is being actively conducted.

Lithium secondary batteries include a cathode, an anode, an electrolyte providing a pathway for the movement of lithium ions between the cathode and the anode, and a separator. Electrical energy is generated by oxidation and reduction reactions when lithium ions are intercalated and de-intercalated at the cathode and anode.

Lithium secondary batteries have an average discharge voltage of about 3.6 to 3.7 V, presenting an advantage in that the discharge voltage thereof is higher than other alkaline batteries and nickel-cadmium batteries. In order to achieve such a high driving voltage, an electrolyte composition which is electrochemically stable at a charge-discharge voltage range of 0 to 4.2V is required.

At the time of initial charging of a lithium secondary battery, lithium ions generated from a cathode active material such as a lithium metal oxide, or the like, migrate to an anode active material such as a graphite-based material, or the like, and are intercalated between layers of the anode active material. Herein, since lithium is highly reactive, it reacts with an electrolyte and the carbon composing the anode active material on the surface of the anode active material (such as a graphite-based material), thereby resulting in the production of a compound such as $Li_2CO_3$, $LiO_2$, or LiOH. These compounds form a solid electrolyte interface (SEI) film on the surface of the anode active material.

The SEI film acts as an ion tunnel and allows only lithium ions to pass through. Since the SEI film has the effect of an ion tunnel, an organic solvent molecule with a high molecular weight moving together with the lithium ions in the electrolyte is inserted between the layers of the anode active material to prevent the anode structure from being destroyed. Therefore, it is possible to prevent contact between the electrolyte and the anode active material, and thus degradation of the electrolyte does not occur and the amount of lithium ions in the electrolyte is reversibly maintained, thereby enabling the charge/discharge to be maintained stably.

In the related art, it is difficult to expect to achieve an improvement in the lifetime characteristics of lithium secondary batteries since an uneven SEI film is formed in the case of employing conventional electrolytes or electrolyte additives. Further, even when the electrolyte includes an electrolyte additive, if the amount of the electrolyte additive is not able to be adjusted to a required amount, problems have been encountered in which the electrolyte additive causes degradation of a cathode surface or an oxidation reaction of the electrolyte during high temperature or high voltage reactions, ultimately resulting in an increase in the irreversible capacity loss of the secondary battery, with deterioration of the lifetime characteristics.

Patent Literature: KR 2009-0026203

SUMMARY

An embodiment of the present invention is directed to providing a novel electrolyte additive.

Another embodiment of the present invention is directed to providing a non-aqueous electrolyte including the electrolyte additive.

Still another embodiment of the present invention is directed to providing a lithium secondary battery which includes a cathode employing a cathode active material, an anode employing an anode active material, a separator interposed between the cathode and the anode, and the non-aqueous electrolyte.

The present invention provides an electrolyte additive comprising a salt of an anion with $K^+$ or $Na^+$, the anion being derived from a nitrogen atom-containing compound, and a lithium-containing compound for forming a coating film.

The present invention provides a non-aqueous electrolyte including a lithium salt, a non-aqueous organic solvent, and the electrolyte additive.

The present invention provides a lithium secondary battery which includes a cathode employing a cathode active material, an anode employing an anode active material, a separator interposed between the cathode and the anode, and the non-aqueous electrolyte.

DETAILED DESCRIPTION OF EMBODIMENTS

Hereinafter, the present disclosure will be described in more detail to assist in understanding the technical idea of the present disclosure.

The terms and words used in the present specification and claims should not be interpreted as being limited to typical meanings or dictionary definitions, but should be interpreted as having meanings and concepts relevant to the technical scope of the present disclosure based on the rule according to which an inventor can appropriately define the concept of the terms in order to describe their own disclosures in best mode.

When a conventional electrolyte or additive is used in a lithium secondary battery, the additive causes degradation of the surface of the cathode and an oxidation reaction of the electrolyte due to an increase in the reactivity between the cathode and the electrolyte, thus resulting in deterioration of the safety and performance of the battery. In particular, when conventionally used additives are stored at a low or high temperature, excessive degradation occurs, leading to the formation of a very thick insulator on the cathode thereby preventing movement of the lithium ions, and thus there is a problem in that the recovery capacity is not generated at all.

However, an electrolyte additive according to an embodiment of the present invention is capable of improving the safety of the battery by reducing the side-reaction activity and the contact surface occurring between the cathode and the electrolyte. Due to characteristics of having a high reaction potential and achieving hardly any change in the reaction potential following cycle progression, it is possible to prevent the deterioration of battery performance due to degradation of additives and the rapid change of reaction potential observed in the related art. Further, the additive forms a stable coating film through the oxidation reaction in the cathode to prevent the degradation of the cathode and suppress elution, and thus it is possible to provide more stable protection of the cathode under a high voltage environment.

Specifically, according to an embodiment of the present invention, an electrolyte additive, which includes a salt of an anion with $K^+$ or $Na^+$, the anion being derived from a nitrogen atom-containing compound, simultaneously includes a lithium-containing compound for formation of a coating film, and thus the salt of the anion derived from a nitrogen atom-containing compound with $K^+$ or $Na^+$ may induce the formation of a more uniform SEI coating film on the anode and cathode formed from the lithium-containing compound. This uniform formation of the coating film facilitates the movement of lithium ions, thus making it possible to secure more improved output characteristics, lifetime characteristics, storage characteristics, and the like.

The electrolyte additive according to an embodiment of the present invention may include the salt of an anion derived from a nitrogen atom-containing compound with $K^+$ or $Na^+$ and a lithium-containing compound for forming a coating film.

The anion derived from a nitrogen atom-containing compound may be one or more selected from a group consisting of amide-based anions, imide-based anions, nitrile-based anions, nitrite anions, and nitrate anions.

Specifically, the amide-based anion may be one or more selected from a group consisting of dimethylformamide anion, dimethylacetamide anion, diethylformamide anion, diethylacetamide anion, methylethylformamide anion, and methylethylacetamide anion.

The imide-based anion may be represented by Chemical Formula 1 below.

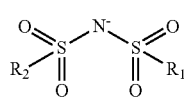
[Chemical Formula 1]

Here, $R_1$ and $R_2$ are each fluoro or $C_1$-$C_4$ fluoroalkyls, or $R_1$ and $R_2$ may be linked to each other to form a ring having a $C_1$-$C_4$ fluoroalkylene group.

The nitrile-based anion may be one or more selected from a group consisting of acetonitrile anion, propionitrile anion, butyronitrile anion, valeronitrile anion, caprylonitrile anion, heptanenitrile anion, cyclopentane carbonitrile anion, cyclohexane carbonitrile anion, 2-fluorobenzonitrile anion, 4-fluorobenzonitrile anion, difluorobenzonitrile anion, trifluorobenzonitrile anion, phenylacetonitrile anion, 2-fluorophenylacetonitrile anion, and 4-fluorophenylacetonitrile anion.

Chemical Formula 1 may have a symmetrical structure. In other words, $R_1$ and $R_2$ may be the same.

Chemical Formula 1 may be one or more selected from a group consisting of Chemical Formulas 2 to 6 below.

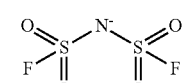
[Chemical Formula 2]

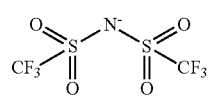
[Chemical Formula 3]

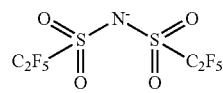
[Chemical Formula 4]

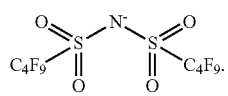
[Chemical Formula 5]

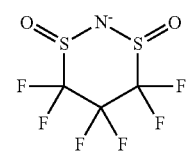
[Chemical Formula 6]

The imide-based anion may include one or more selected from the group consisting of Chemical Formulas 2 to 6 above.

According to an embodiment of the present invention, the salt of the anion derived from the nitrogen atom-containing compound with $K^+$ or $Na^+$ may be one or more selected from a group consisting of potassium bis(fluorosulfonyl)imide, potassium nitrate, sodium bis(fluorosulfonyl)imide, and sodium nitrate.

The lithium-containing compound for forming a coating film is capable of forming a coating film on the cathode and the anode, and is capable of achieving more uniform formation of the film by being included in the electrolyte together with the salt of the anion derived from the nitrogen atom-containing compound with $K^+$ or $Na^+$. The lithium-containing compound for forming a coating film may be one or more selected from a group consisting of $LiPO_2F_2$, LiBOB, LiTFSI, LiFSI, and LiDFOB.

The salt of the anion derived from the nitrogen atom-containing compound with $K^+$ or $Na^+$ may easily induce the formation of coating films on the surfaces of the cathode and the anode in the electrolyte.

In general, in an environment where a secondary battery is repeatedly charged and discharged, an oxidation reaction proceeds on the surface of the cathode, and a reduction reaction proceeds on the surface of the anode. The electrolyte additive according to an embodiment of the present invention may form coating films on the surfaces of the cathode and the anode to effectively control the elution of lithium ions generated from the cathode and to prevent the cathode from being degraded. More specifically, the film formed by the electrolyte additive on the surface of the anode is partially degraded through a reduction reaction at the time of charging and discharging the battery, but the degraded electrolyte additive may move to the surface of the cathode again to form the coating film on the surface of the cathode again through an oxidation reaction.

Therefore, even when charging and discharging actions are repeated several times, the additive may maintain the coating film on the surface of the cathode to effectively prevent excessive elution of lithium ions from the cathode. This is presumably resulted from the chemical properties of $K^+$ or $Na^+$ included in the electrolyte additive as an ion of an alkaline group element, which is similar to $Li^+$ present in the cathode and the anode. Therefore, the lithium secondary battery according to an embodiment of the present disclosure may achieve improved high temperature and low temperature lifetime characteristics through maintenance of and preventing degradation of the structure of the cathode, even when the cathode is repeatedly charged and discharged.

In addition, the present invention may provide a non-aqueous electrolyte including: a lithium salt, a non-aqueous organic solvent, and the electrolyte additive as described above.

The electrolyte additive may include the salt of the anion derived from a nitrogen atom-containing compound with $K^+$ or $Na^+$ and the lithium-containing compound for forming a coating film at a weight ratio of 1:0.5 to 4. When the weight ratio between the salt of the anion derived from the nitrogen atom-containing compound with $K^+$ or $Na^+$ and the lithium-containing compound for forming a coating film is lower than 1:0.5, the SEI coating film may not be efficiently formed on the cathode and the anode. When the weight ratio thereof is higher than 1:4, the movement of lithium ions may rather be hindered due to excessive formation of coating film.

According to an embodiment of the present invention, the content of the electrolyte additive may be 0.05 to 10 wt % based on a total amount of the non-aqueous electrolyte. Preferably, the content of the electrolyte additive may be 0.1 to 3 wt % based on the total amount of the non-aqueous electrolyte. When the content of the electrolyte additive is less than 0.05 wt %, improvement in the low temperature and high temperature storage characteristics and the high temperature lifetime characteristics of the lithium secondary battery may be insignificant. When the content of the electrolyte additive exceeds 10 wt %, resistance may increase due to excessive formation of the coating film.

In particular, when the electrolyte additive is applied to a lithium secondary battery, the salt with $K^+$ or $Na^+$ may be included to improve the low temperature and high temperature storage characteristics as well as the high temperature lifetime characteristics, and to secure stability of the secondary battery formed by minimizing the rate of change of the thickness. Particularly, in addition to an effect of improving the lifetime and resistance characteristics of the secondary battery at high temperature, the high temperature output characteristics of the secondary battery can also be secured due to the uniform formation of the coating film.

The lithium salt may include a lithium salt commonly used in the art, and may include, for example, one, or mixture of two or more selected from a group consisting of $LiPF_6$, $LiAsF_6$, $LiBF_4$, $LiSbF_6$, $LiAlO_4$, $LiAlCl_4$, and $LiClO_4$.

The concentration of the lithium salt in the non-aqueous electrolyte is preferably 0.01 mol/L to 2 mol/L, and more preferably, 0.01 mol/L to 1 mol/L.

For the non-aqueous organic solvent used in the present disclosure, organic solvents commonly used in electrolytes for lithium secondary batteries may be used without limitation, and for example, ether, ester, amide, linear carbonate, cyclic carbonate, phosphate-based solvent, nitrile-based solvent, fluorinated ether-based solvent, aromatic-based solvent, fluorinated aromatic-based solvent, and the like, may be used alone or in combination of two or more.

Among these non-aqueous organic solvents, representatively, a carbonate compound which is a cyclic carbonate, a linear carbonate or a mixture thereof may be included. The cyclic carbonate compound may include without limitation, one of, or a mixture of two or more of the compounds selected from a group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and a halide thereof.

The linear carbonate compound may be one of, or a mixture of two or more of the compounds selected from a group consisting of dimethyl carbonate (DMC), diethyl carbonate (DEC), dipropyl carbonate (DPC), ethyl methyl carbonate (EMC), methyl propyl carbonate (MPC), and ethyl propyl carbonate, but the linear carbonate compound is not limited thereto.

In particular, the cyclic carbonate preferably contains at least one selected from a group consisting of propylene carbonate, ethylene carbonate, or a mixture thereof, which are high-viscosity organic solvents and have high permittivity to dissociate the lithium salt well in the electrolyte.

Further, it is preferable to use a mixture of the cyclic carbonate with the linear carbonate of at least one selected from a group consisting of diethyl carbonate, dimethyl carbonate, ethyl methyl carbonate or a mixture thereof. This is because mixing with a linear carbonate having low viscosity and low permittivity, as above, at an appropriate ratio enables the preparation of an electrolyte having a high electric conductivity. The cyclic carbonate and the linear carbonate can be mixed at weight ratios from 1:9 to 9:1.

The ester may include one, or mixture of two or more selected from a group consisting of methyl acetate, ethyl acetate, propyl acetate, ethyl propionate (EP), propyl propionate, methyl propionate (MP), γ-butyrolactone, γ-valerolactone, γ-caprolactone, δ-valerolactone, and ε-caprolactone. However, among these examples, particularly, it is preferable to include at least one selected from a group consisting ethyl propionate (EP), propyl propionate, methyl propionate (MP), which have low viscosity, or a mixture thereof.

The phosphoric acid-based solvent and nitrile-based solvent may be substituted with a fluorine (F). When the phosphoric acid-based solvent and nitrile-based solvent are substituted with a fluorine element, a great increase in the flame retardancy is observed. However, when the solvent is substituted with Cl, Br, I, or the like, the reactivity of the solvent increases together, which is not preferable as an electrolyte.

The phosphate-based solvent may include trimethylphosphine oxide, triethylphosphine oxide, tripropylphosphine oxide, triphenylphosphine oxide, diethyl methylphosphonate, dimethyl methylphosphonate, diphenyl methylphosphonate, bis(2,2,2-trifluoroethyl) methylphosphonate, trimethyl phosphate, triethyl phosphate, tripropyl phosphate, ethyl methyl phenyl phosphate, and the like. These phosphate-based solvents may be used alone or in a combination of two or more.

The nitrile-based solvent may include acetonitrile, propionitrile, butyronitrile, valeronitrile, caprilonitrile, heptanenitrile, cyclopentanecarbonitrile, cyclohexanecarbonitrile, 2-fluorobenzonitrile, 4-fluorobenzonitrile, difluorobenzonitrile, trifluorobenzonitrile, phenylacetonitrile, 2-fluorophenylacetonitrile, 4-fluorophenylacetonitrile, and the like. These nitrile-based solvents may be used alone or in a combination of two or more.

The fluorinated ether-based solvent may include bis-2,2-trifluoroethyl ether, n-butyl-1,1,2,2-tetrafluoroethyl ether, 2,2,3,3,3-pentafluoropropyl methyl ether, 2,2,3,3,3-pentafluoropropyl, 1,1,2,2-tetrafluoro ethyl ether, 1,1,2,2-tetrafluoroethyl methyl ether, 1,1,2,2-tetrafluoroethyl ethyl ether, trifluoroethyl dodecafluorohexyl ether, and the like. These fluorinated ether-based solvents may be used alone or in a combination of two or more thereof.

The aromatic solvent may include halogenated benzene compounds such as chlorobenzene, chlorotoluene, fluorobenzene, and the like, and alkylated aromatic compounds such as tert-butylbenzene, tert-pentylbenzene, cyclohexylbenzene, biphenyl, terphenyl, and the like. An alkyl group of the alkylated aromatic compound may be halogenated, and as an example thereof, a fluorinated aromatic compound may be included. Examples of the halogenated aromatic-based compound may include trifluoromethoxy benzene, and the like.

Meanwhile, the present invention may provide a lithium secondary battery including a cathode employing a cathode active material, an anode employing an anode active material, a separator interposed between the cathode and the anode, and the non-aqueous electrolyte.

Any cathode active material may be used without limitation if it is a compound capable of reversibly intercalating/de-intercalating lithium.

In the lithium secondary battery according to the embodiment of the present disclosure, the cathode active material may include one or more selected from a group consisting of spinel lithium transition metal oxides having a hexagonal layered rock-salt structure with high capacity characteristics, an olivine structure, and a cubic structure, $V_2O_5$, TiS, and MoS. More specifically, the cathode active material may include, for example, one of, or mixture of two or more of the compounds selected from the compounds represented by the Chemical Formulas 7 to 9 below:

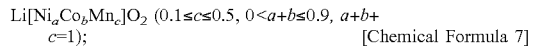

$Li[Ni_aCo_bMn_c]O_2$ ($0.1 \leq c \leq 0.5$, $0 < a+b \leq 0.9$, $a+b+c=1$); [Chemical Formula 7]

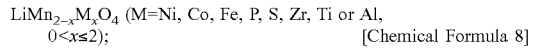

$LiMn_{2-x}M_xO_4$ (M=Ni, Co, Fe, P, S, Zr, Ti or Al, $0 < x \leq 2$); [Chemical Formula 8]

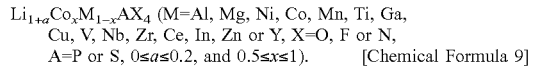

$Li_{1+a}Co_xM_{1-x}AX_4$ (M=Al, Mg, Ni, Co, Mn, Ti, Ga, Cu, V, Nb, Zr, Ce, In, Zn or Y, X=O, F or N, A=P or S, $0 \leq a \leq 0.2$, and $0.5 \leq x \leq 1$). [Chemical Formula 9]

The cathode active material may preferably include at least one, or a mixture of two or more selected from a group consisting of $Li[Ni_{0.6}Co_{0.2}Mn_{0.2}]O_2$, $Li[Ni_{0.5}Co_{0.2}Mn_{0.3}]O_2$, $Li[Ni_{1/3}Co_{1/3}Mn_{1/3}]O_2$ and $LiCoO_2$.

According to a particularly preferable embodiment, $Li[Ni_aCo_bMn_c]O_2$ may be used for the cathode to thereby achieve a synergistic effect in combination with the compound described in Chemical Formula 1 of the present disclosure. When cathode active material of the lithium-nickel-manganese-cobalt-based oxide is employed, it may have an unstable structure due to cationic mixing in which Li monovalent ions ($Li^+$) and Ni divalent ions ($Ni^{+2}$) are switched in a layered structure of the cathode active material during the charge/discharge process as the content of Ni in transition metals increases, and thus the cathode active material causes a side reaction with the electrolyte, or elution of the transition metal, or the like, to occur. Therefore, when the electrolyte additive according to an embodiment of the present disclosure is used, the cation mixing of the ions can be minimized.

The anode active material includes amorphous carbon or crystalline carbon, and specific examples thereof may include carbons such as non-graphitizable carbon, graphite-based carbon, and the like; metal complex oxides such as $Li_xFe_2O_3$ ($0 \leq x \leq 1$), $Li_xWO_2$ ($0 \leq x \leq 1$), $Sn_xMe_{1-x}Me'_yO_z$ (Me=Mn, Fe, Pb or Ge; Me'=Al, B, P, Si, Group 1, Group 2, Group 3 elements of the periodic table or halogen; $0 < x \leq 1$; $1 \leq y \leq 3$; $1 \leq z \leq 8$), and the like; lithium metal; lithium alloy; silicon-based alloy; tin-based alloy; oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$ or $Bi_2O_5$, and the like; conductive polymers such as polyacetylene, and the like; Li—Co—Ni-based materials, and the like.

In addition, the separator may be produced by using a porous polymer film, for example, made of a polyolefin-based polymer such as an ethylene homopolymer, a propylene homopolymer, an ethylene/butene copolymer, an ethylene/hexene copolymer, an ethylene/methacrylate copolymer, or the like, alone, or composed by stacking two or more porous polymer films. In addition, a non-woven fabric made of a conventional porous non-woven fabric, for example, a glass fiber having a high melting point, polyethylene terephthalate fiber, or the like, may be used, but the separator is not limited thereto.

The cathode and/or the anode may be produced by mixing and stirring a binder and a solvent, and if necessary, a conventionally usable conductive agent and a dispersant to prepare a slurry, and then applying and compressing the slurry to a current collector.

Examples of the binder may include polyvinylidene fluoride-hexafluoropropylene copolymer (PVDF-co-HEP), polyvinylidene fluoride, polyacrylonitrile, polymethylmethacrylate, polyvinyl alcohol, carboxymethyl cellulose (CMC), starch, hydroxypropyl cellulose, regenerated cellulose, polyvinylpyrrolidone, tetrafluoroethylene, polyethylene, polypropylene, polyacrylic acid, ethylene-propylene-diene monomer (EPDM), sulfonated EPDM, styrene butylene rubber (SBR), fluorine rubber, various copolymers, and the like.

According to an embodiment of the present disclosure, the lithium secondary battery including the electrolyte additive may be subjected to a formation and aging processes to secure the performance of the secondary battery.

The formation process activates the battery by repeating the charging and discharging process after assembly of the secondary battery, wherein lithium ions from a lithium metal oxide used as a cathode during charging are migrated and intercalated into a carbon electrode used as an anode, and lithium has strong reactivity to react with the carbon anode to produce compounds such as $Li_2CO_3$, LiO, and LiOH, and the like, which form a solid electrolyte interface (SEI) coating film on the surface of the anode. In addition, the aging process stabilizes the activated battery by allowing the battery to stand for a predetermined period of time.

The SEI film is formed on the surface of the anode through the above-described formation process. It is general that the SEI film is stabilized by a room temperature aging process, i.e., by allowing the battery to stand at room temperature for a predetermined period of time. It may be confirmed that not only during the room temperature aging process, but also even if a high temperature aging process is performed, the lithium secondary battery using the non-aqueous electrolyte including the electrolyte additive according to the embodiment of the present disclosure may not experience problems such as reduction in the stability of the SEI film, degradation thereof, and the like, due to the high temperature or because of the K and Na, which are homologous elements as lithium.

The formation process is not particularly limited, and the battery may be half-charged from 1.0 to 3.8 V or fully charged at 3.8 to 4.3 V. Further, the battery may be charged at a current density of 0.1 C to 2 C (c-rate) for about 5 minutes to 1 hour.

The aging process may be performed at room temperature or at a temperature range of 45 to 100° C. (high temperature). If the temperature exceeds 100° C., it is possible that an exterior material may be ruptured or the battery may be ignited due to evaporation of the electrolyte. Further, the remaining capacity (state of charge: SOC) of the battery may be in any range from 100%, which is a fully charged state, to 0% due to the discharge. In addition, the storage time is not particularly limited, but is preferably to set the time from about 1 hour to 1 week.

The external shape of the lithium secondary battery according to an embodiment of the present disclosure is not particularly limited, but it may be employed as a cylindrical shape using a can, a prismatic shape, a pouch shape, a coin shape, or the like.

Hereinafter, the present disclosure is described in detail with reference to Examples. However, the following Examples according to the present disclosure may be modified into various embodiments, and should not be interpreted as limiting the scope of the present disclosure. These Examples of the present disclosure are provided so that those skilled in the art may gain a more thorough understanding of the present disclosure.

EXAMPLE

Example 1

[Preparation of Electrolyte]

A non-aqueous electrolyte was prepared by adding a non-aqueous organic solvent having a composition of ethylene carbonate (EC), ethyl methyl carbonate (EMC), and diethyl carbonate (DEC) at a volume ratio of 25:45:30, and $LiPF_6$ as a lithium salt in an amount of 1.0 mol/L based on the total amount of the non-aqueous electrolyte, and by adding 0.5 wt % of potassium bis(fluorosulfonyl)imide and 0.5 wt % of $LiPO_2F_2$ (weight ratio of 1:1) based on the total amount of the non-aqueous electrolyte, as an electrolyte additive.

[Manufacture of Lithium Secondary Battery]

A cathode mixture slurry was prepared by adding 92 wt % of $Li(Ni_{0.5}Co_{0.2}Mn_{0.3})O_2$ as a cathode active material, 4 wt % of carbon black as a conductive agent, and 4 wt % of polyvinylidene fluoride (PVDF) as a binder, to N-methyl-2-pyrrolidone (NMP) as a solvent. The cathode mixture slurry was applied onto an aluminum (Al) thin film as a cathode current collector with a thickness of about 20 µm and dried to produce a cathode, followed by employment of a roll press to complete the cathode.

Further, an anode mixture slurry was prepared by adding 96 wt % of carbon powder as an anode active material, 3 wt % of PVDF as a binder, and 1 wt % of carbon black as a conductive agent, to NMP as a solvent. The anode mixture slurry was applied onto a copper (Cu) thin film as an anode current collector with a thickness of 10 µm and dried to produce an anode, followed by employment of a roll press to complete the anode.

A pouch-type battery was manufactured by a conventional method using the cathode and anode together with a separator composed of three layers of polypropylene/polyethylene/polypropylene (PP/PE/PP), and the prepared non-aqueous electrolyte was then injected into the battery to manufacture a lithium secondary battery.

Example 2

A non-aqueous electrolyte and a lithium secondary battery were manufactured in the same manner as in Example 1, except that 0.5 wt % of potassium bis(fluorosulfonyl)imide and 1.0 wt % of $LiPO_2F_2$ (weight ratio 1:2) were included as an electrolyte additive.

Example 3

A non-aqueous electrolyte and a lithium secondary battery were manufactured in the same manner as in Example 1, except that 0.5 wt % of potassium bis(fluorosulfonyl)imide and 1.5 wt % of $LiPO_2F_2$ (weight ratio 1:3) were included as an electrolyte additive.

Example 4

A non-aqueous electrolyte and a lithium secondary battery were manufactured in the same manner as in Example 1, except that 1.0 wt % of potassium bis(fluorosulfonyl)imide and 0.5 wt % of $LiPO_2F_2$ (weight ratio 1:0.5) were included as an electrolyte additive.

Example 5

A non-aqueous electrolyte and a lithium secondary battery were manufactured in the same manner as in Example 1, except that 0.5 wt % of sodium bis(fluorosulfonyl)imide and 0.5 wt % of $LiPO_2F_2$ (weight ratio 1:1) were included as an electrolyte additive.

Example 6

A non-aqueous electrolyte and a lithium secondary battery were manufactured in the same manner as in Example 1, except that 0.5 wt % of sodium bis(fluorosulfonyl)imide and 1.0 wt % of $LiPO_2F_2$ (weight ratio 1:2) were included as an electrolyte additive.

Example 7

A non-aqueous electrolyte and a lithium secondary battery were manufactured in the same manner as in Example 1, except that 0.5 wt % of potassium bis(trifluorosulfonyl)imide and 1.0 wt % of $LiPO_2F_2$ (weight ratio 1:2) were included as an electrolyte additive.

Example 8

A non-aqueous electrolyte and a lithium secondary battery were manufactured in the same manner as in Example 1, except that 0.5 wt % of sodium bis(trifluorosulfonyl)imide and 1.0 wt % of $LiPO_2F_2$ (weight ratio 1:2) were included as an electrolyte additive.

Comparative Example 1

A non-aqueous electrolyte and a lithium secondary battery were manufactured in the same manner as in Example 1, except that 0.5 wt % of potassium bis(fluorosulfonyl)imide was included as an electrolyte additive.

Comparative Example 2

A non-aqueous electrolyte and a lithium secondary battery were manufactured in the same manner as in Example 1, except that 1.0 wt % of $LiPO_2F_2$ was included as an electrolyte additive.

Comparative Example 3

A non-aqueous electrolyte and a lithium secondary battery were manufactured in the same manner as in Example 1, except that 0.5 wt % of lithium bis(fluorosulfonyl)imide and 1.0 wt % of $LiPO_2F_2$ (weight ratio 1:2) were included as an electrolyte additive.

Comparative Example 4

A non-aqueous electrolyte and a lithium secondary battery were manufactured in the same manner as in Example 1, except that 0.5 wt % of lithium bis(trifluorosulfonyl)imide and 1.0 wt % of $LiPO_2F_2$ (weight ratio 1:2) were included as an electrolyte additive.

Experimental Example

High Temperature Lifetime Evaluation

The lithium secondary test batteries were charged at a constant current until the voltage reached 4.20 V (vs. Li) at a current of 1.0 C rate at high temperature (45° C.) Subsequently, the lithium secondary batteries were cut-off at a current of 0.05 C rate while maintaining 4.20 V in a constant voltage mode. Then, the batteries were discharged at a constant current of 1.0 C rate until the voltage reached 3.0 V (vs. Li) (1st cycle) at the time of discharging the batteries. The above-described cycle was repeated up to 300 cycles. The results of the above-described experiment are shown in Table 1 below.

TABLE 1

| | High Temperature Lifetime Characteristics | | |
|---|---|---|---|
| Test Subject | Initial Cycle Capacity (mAh) | 300$^{th}$ Cycle Capacity (mAh) | Capacity Retention Rate (%) 300$^{th}$ Cycle Capacity/Initial Cycle Capacity * 100 (%) |
| Example 1 | 628.4 | 531.8 | 84.6 |
| Example 2 | 627.9 | 536.7 | 85.5 |
| Example 3 | 625.6 | 535.4 | 85.6 |
| Example 4 | 624.1 | 529.1 | 84.8 |
| Example 5 | 623.3 | 517.2 | 83.0 |
| Example 6 | 624.8 | 520.1 | 83.2 |
| Example 7 | 626.7 | 528.1 | 84.3 |
| Example 8 | 622.9 | 518.4 | 83.2 |
| Comparative Example 1 | 623.1 | 474.2 | 76.1 |
| Comparative Example 2 | 621.8 | 479.8 | 77.2 |
| Comparative Example 3 | 628.4 | 531.8 | 84.6 |
| Comparative Example 4 | 627.9 | 536.7 | 85.5 |

Capacity Evaluation by High Temperature Storage

The lithium secondary batteries manufactured using the non-aqueous electrolytes of the Examples above were charged to 4.2 V at a current of 1 C rate at room temperature (25° C.), and discharged to 3.0 V at a current of 1 C rate to measure the discharge capacity. The batteries were charged again to 4.2 V in the same manner and stored in a chamber at 60° C. for 30 days. Then, the batteries were discharged to 3.0 V at a current of 1 C rate at room temperature, aged for 1 hour, charged again to 4.2 V at a current of 1 C rate, and discharged to 3.0 V at a current of 1 C rate to measure the discharge capacity. The measured discharge capacity was compared with the discharge capacity value measured initially. The charge and discharge experiment results are shown in Table 2.

TABLE 2

| | High Temperature Storage Characteristics (60° C.) | | |
|---|---|---|---|
| Test Subject | Initial Discharge Capacity (mAh) | Discharge Capacity After Standing 30 Days (mAh) | Capacity Retention Rate (%) Capacity After Standing 30 Days/ Initial Capacity * 100 (%) |
| Example 1 | 621.4 | 508.0 | 81.8 |
| Example 2 | 620.2 | 511.8 | 82.5 |
| Example 3 | 617.8 | 510.9 | 82.7 |
| Example 4 | 619.2 | 511.4 | 82.6 |
| Example 5 | 617.6 | 490.4 | 79.4 |
| Example 6 | 614.2 | 493.3 | 80.3 |
| Example 7 | 613.6 | 503.2 | 82.0 |
| Example 8 | 615.7 | 484.1 | 78.6 |
| Comparative Example 1 | 612.9 | 410.4 | 67.0 |
| Comparative Example 2 | 614.3 | 460.1 | 74.9 |
| Comparative Example 3 | 617.2 | 458.2 | 74.2 |
| Comparative Example 4 | 615.3 | 455.9 | 74.1 |

Resistance Evaluation by High Temperature Storage

The secondary batteries manufactured by non-aqueous electrolyte of the Examples and Comparative Examples were placed in a chamber maintained at 25° C., and subjected to charge/discharge tests as follows using a charge/discharge device. First, the secondary batteries were charged up to 60% of SOC (state of charge) at 1 C, and then discharged/charged at 0.2 C for 10 seconds. Next, the batteries were discharged/charged at 0.5 C for 10 seconds. Thereafter, the secondary batteries were discharged and charged for 10 seconds in the same manner as above in the following order of 1 C, 2 C, and 3 C. Finally, the secondary batteries were charged at a current of 0.5 C to a voltage of 4.2 V. The initial impedance (DC-IR) was determined by calculating the slope of a trend line of a voltage-to-current graph constructed using the voltage values measured after discharging the batteries at 0.2 C, 0.5 C, 1 C, 2 C, and 3 C. After measuring the initial impedance, the batteries were placed in a chamber maintained at 60° C., and the impedance thereof was measured after 30 days to calculate the impedance (DC-IR). Results thereof are shown in Table 3 below.

TABLE 3

| | High Temperature Storage Characteristics (60° C.) | | |
|---|---|---|---|
| Test Subject | Initial Impedance (mΩ) | Impedance After 60° C. Storage (mΩ) (after 4 W) | Change Rate (%) After 60° C. (mΩ)/ Initial Impedance (mΩ) * 100 (%) |
| Example 1 | 33.2 | 42.1 | 126.8 |
| Example 2 | 32.7 | 38.7 | 118.3 |
| Example 3 | 33.6 | 39.9 | 118.8 |
| Example 4 | 33.1 | 43.3 | 130.8 |
| Example 5 | 37.4 | 52.1 | 139.3 |
| Example 6 | 38.1 | 49.3 | 129.4 |
| Example 7 | 34.5 | 44 | 127.5 |

TABLE 3-continued

High Temperature Storage Characteristics (60° C.)

| Test Subject | Initial Impedance (mΩ) | Impedance After 60° C. Storage (mΩ) (after 4 W) | Change Rate (%) After 60° C. (mΩ)/ Initial Impedance (mΩ) * 100 (%) |
|---|---|---|---|
| Example 8 | 38.7 | 54.1 | 139.8 |
| Comparative Example 1 | 36.2 | 59.1 | 163.3 |
| Comparative Example 2 | 38.1 | 68.9 | 180.8 |
| Comparative Example 3 | 41.4 | 71.5 | 172.7 |
| Comparative Example 4 | 33.2 | 42.1 | 126.8 |

Measurement of Thickness Change Rate

Experiments were performed to check the thickness change rates of the secondary batteries manufactured using the non-aqueous electrolytes of the Examples and Comparative Examples.

The batteries were charged at a constant current of 1.0 C rate at a high temperature (45° C.) until the voltage reached 4.20 V (vs. Li), and then cut off at a current of 0.05 C rate while maintaining 4.20 V in a constant voltage mode. Then, after discharging the batteries at a constant current of 1.0 C rate until the voltage reached 3.0 V (vs. Li) at the time of discharge, the electrode thickness of the $1^{st}$ cycle was measured. Next, the above-described charge and discharge processes was repeated, and the electrode thickness was measured after the $300^{th}$ cycle for comparison with the initial electrode thickness at the $1^{st}$ cycle. Results are shown in Table 4 below.

*Thickness Change Rate: (electrode thickness after $300^{th}$ cycle–electrode thickness before $1^{st}$ cycle)/electrode thickness before $1^{st}$ cycle×100

TABLE 4

| Test Subject | Thickness Change Rate (%) |
|---|---|
| Example 1 | 5.3 |
| Example 2 | 4.9 |
| Example 3 | 4.3 |
| Example 4 | 4.7 |
| Example 5 | 7.1 |
| Example 6 | 7.7 |
| Example 7 | 5.9 |
| Example 8 | 8.2 |
| Comparative Example 1 | 9.5 |
| Comparative Example 2 | 12.2 |
| Comparative Example 3 | 13.4 |
| Comparative Example 4 | 5.3 |

As can be confirmed from the results of testing using the above examples and comparative examples, the lithium secondary batteries of the present invention were generally excellent in the areas of high temperature lifetime characteristics, high-temperature storage characteristics, and thickness change rate.

Secondary batteries formed by including the electrolyte additive according to an embodiment of the present invention may have excellent high-temperature output characteristics and high-temperature lifetime efficiency, and superior high-temperature storage characteristics and thickness change rate.

What is claimed is:

1. An electrolyte additive comprising:
   a salt of an anion with $K^+$ or $Na^+$, the anion being derived from a nitrogen atom-containing compound, and
   a lithium-containing compound for forming a coating film,
   wherein the anion derived from a nitrogen atom-containing compound is at least one selected from the group consisting of amide-based anion, imide-based anion, nitrile-based anion, nitrite anion, and nitrate anion,
   wherein the amide-based anion is represented by Chemical Formula 1 below:

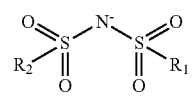

[Chemical Formula 1]

in Chemical Formula 1, $R_1$ and $R_2$ are each fluoro or $C_1$-$C_4$ fluoroalkyls, or $R_1$ and $R_2$ may be linked to each other to form a ring having a $C_1$-$C_4$ fluoroalkylene group,
   wherein the lithium-containing compound for forming a coating film is at least one selected from the group consisting of $LiPO_2F_2$, LiBOB, LiTFSI, LiFSI, and LiDFOB,
   wherein a weight ratio of the salt of the anion derived from the nitrogen atom-containing compound with $K^+$ or $Na^+$ and the lithium-containing compound for forming a coating film is 1:0.5 to 1:4.

2. The electrolyte additive of claim 1, wherein the amide-based anion is at least one selected from the group consisting of dimethylformamide anion, dimethylacetamide anion, diethylformamide anion, diethylacetamide anion, methylethylformamide anion, and methylethylacetamide anion.

3. The electrolyte additive of claim 2, wherein the nitrile-based anion is at least one selected from the group consisting of acetonitrile anion, propionitrile anion, butyronitrile anion, valeronitrile anion, caprylonitrile anion, heptanenitrile anion, cyclopentane carbonitrile anion, cyclohexane carbonitrile anion, 2-fluorobenzonitrile anion, 4-fluorobenzonitrile anion, difluorobenzonitrile anion, trifluorobenzonitrile anion, phenylacetonitrile anion, 2-fluorophenylacetonitrile anion, and 4-fluorophenylacetonitrile anion.

4. The electrolyte additive of claim 1, wherein the Chemical Formula 1 is at least one selected from the group consisting of Chemical Formulas 2 to 6 below:

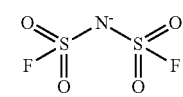

[Chemical Formula 2]

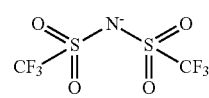

[Chemical Formula 3]

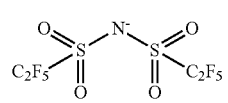

[Chemical Formula 4]

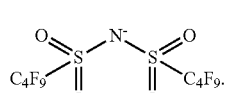

[Chemical Formula 5]

5. The electrolyte additive of claim 1, wherein the salt of the anion derived from the nitrogen atom-containing compound with $K^+$ or $Na^+$ is at least one selected from the group consisting of potassium bis(fluorosulfonyl)imide, potassium nitrate, sodium bis(fluorosulfonyl)imide, and sodium nitrate.

6. A non-aqueous electrolyte comprising:
 a lithium salt,
 a non-aqueous organic solvent, and
 the electrolyte additive of claim 1.

7. The non-aqueous electrolyte of claim 6, wherein the electrolyte additive is included at 0.05 to 10 wt % based on a total amount of the non-aqueous electrolyte.

8. The non-aqueous electrolyte of claim 6, wherein the lithium salt is at least one selected from the group consisting of $LiPF_6$, $LiAsF_6$, $LiBF_4$, $LiSbF_6$, $LiAlO_4$, $LiAlCl_4$, and $LiClO_4$.

9. The non-aqueous electrolyte of claim 6, wherein the non-aqueous organic solvent is at least one selected from ether, ester, amide, linear carbonate, cyclic carbonate, phosphate-based solvent, nitrile-based solvent, fluorinated ether-based solvent, aromatic-base solvent, and fluorinated aromatic-based solvent.

10. A lithium secondary battery comprising:
 a cathode employing a cathode active material,
 an anode employing an anode active material,
 a separator interposed between the cathode and the anode, and
 the non-aqueous electrolyte of claim 6.

\* \* \* \* \*